US 6,726,700 B1

(12) United States Patent
Levine

(10) Patent No.: US 6,726,700 B1
(45) Date of Patent: *Apr. 27, 2004

(54) MANIPULATABLE DELIVERY CATHETER FOR OCCLUSIVE DEVICES

(75) Inventor: Marc-Alan Levine, San Francisco, CA (US)

(73) Assignee: Counter Clockwise, Inc., San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 171 days.

(21) Appl. No.: 09/643,085

(22) Filed: Aug. 21, 2000

(51) Int. Cl.[7] .............................................. A61M 29/00
(52) U.S. Cl. ........................ 606/194; 606/194; 606/200
(58) Field of Search ................................. 606/191–195, 606/200, 201, 108, 14; 604/95.03, 96.01, 101.04, 103.04, 103.09, 103.11–103.14, 523, 525–528, 915, 102.01; 623/1.11; 600/373, 434, 486; 148/519, 537

(56) References Cited

U.S. PATENT DOCUMENTS

| | | | |
|---|---|---|---|
| 3,470,876 A | | 10/1969 | Barchilon |
| 4,150,676 A | | 4/1979 | Jackson |
| 4,249,536 A | * | 2/1981 | Vega ............................ 604/103 |
| 4,284,459 A | | 8/1981 | Patel et al. |
| 4,586,923 A | | 5/1986 | Gould et al. |
| 4,589,410 A | | 5/1986 | Miller |
| 4,685,457 A | | 8/1987 | Donenfeld |
| 4,723,936 A | * | 2/1988 | Buchbinder et al. ...... 604/95.01 |
| 4,739,768 A | | 4/1988 | Engelson |
| 4,748,982 A | | 6/1988 | Horzewski et al. |
| 4,798,598 A | | 1/1989 | Bonello et al. |
| 4,802,490 A | * | 2/1989 | Johnston ..................... 600/454 |
| 4,813,934 A | | 3/1989 | Engelson et al. |
| 4,884,579 A | | 12/1989 | Engelson |
| 4,898,577 A | | 2/1990 | Badger et al. |
| 4,960,411 A | * | 10/1990 | Buchbinder .............. 604/95.01 |
| 4,964,409 A | * | 10/1990 | Tremulis .................... 600/434 |
| 4,976,688 A | | 12/1990 | Rosenblum |
| 4,983,169 A | | 1/1991 | Furukawa |
| 4,994,069 A | | 2/1991 | Ritchart et al. |
| 5,114,414 A | | 5/1992 | Buchbinder |

(List continued on next page.)

FOREIGN PATENT DOCUMENTS

| | | |
|---|---|---|
| CA | 1 262 854 | 11/1989 |
| DE | 199 49 590 | 6/2000 |
| EP | 0 900 575 A1 | 3/1999 |
| WO | WO 01/03766 | 1/2001 |

OTHER PUBLICATIONS

English Abstract of German Patent Publication No. 199 49 590 A1 published on Jun. 21, 2002 located in Dialog®, File 351, Derwent WPI© 2002, one page.

Primary Examiner—Vy Q. Bui
(74) Attorney, Agent, or Firm—Morrison & Forester LLP

(57) ABSTRACT

This is in the general field of surgical instruments and is, specifically, a microballoon-tipped delivery catheter with a flexible, proximally-manipulated hinge or joint region. The catheter may have a shaft of varying flexibility which contains several lumen. The inner, or delivery, lumen generally may be used with a guide wire to access target sites within the body via the flexible, small diameter vessels of the body. The delivery lumen may be also used for placement of occlusive materials, e.g., in an aneurysm. Inflation of the micro-balloon, located near the distal tip of the catheter, is effected using the inflation lumen. The push/pull wire lumen contains a wire, which when manipulated, flexes the catheter's distal tip.

29 Claims, 9 Drawing Sheets

U.S. PATENT DOCUMENTS

| | | |
|---|---|---|
| 5,125,896 A | 6/1992 | Hojeibane |
| 5,273,535 A | 12/1993 | Edwards et al. |
| 5,318,525 A | 6/1994 | West et al. |
| 5,327,905 A | 7/1994 | Avitall |
| 5,345,937 A | 9/1994 | Middleman et al. |
| 5,368,564 A | 11/1994 | Savage |
| 5,368,592 A | 11/1994 | Stern et al. |
| 5,383,852 A | 1/1995 | Stevens-Wright |
| 5,391,146 A | 2/1995 | That et al. |
| 5,391,147 A | 2/1995 | Imran et al. |
| 5,429,604 A | 7/1995 | Hammersmark et al. |
| 5,431,168 A | 7/1995 | Webster, Jr. |
| 5,437,632 A | 8/1995 | Engelson |
| 5,478,330 A | 12/1995 | Imran et al. |
| 5,480,382 A | 1/1996 | Hammerslag et al. |
| 5,484,407 A | 1/1996 | Osypka |
| 5,487,757 A | 1/1996 | Truckai et al. |
| 5,499,973 A | 3/1996 | Saab |
| 5,588,964 A | 12/1996 | Imran et al. |
| 5,715,817 A | 2/1998 | Stevens-Wright et al. |
| 5,810,757 A * | 9/1998 | Sweezer et al. ............ 604/523 |
| 5,826,576 A | 10/1998 | West |
| 5,865,800 A | 2/1999 | Mirarchi et al. |
| 5,868,702 A | 2/1999 | Stevens et al. |
| 5,906,590 A | 5/1999 | Hunjan et al. |
| 5,908,405 A | 6/1999 | Imran et al. |
| 5,911,715 A | 6/1999 | Berg et al. |
| 5,916,214 A | 6/1999 | Cosio et al. |
| 5,968,012 A | 10/1999 | Ren et al. |
| 6,036,717 A | 3/2000 | Mers Kelly et al. |
| 6,071,279 A | 6/2000 | Whayne et al. |
| 6,074,407 A * | 6/2000 | Levine et al. ............... 606/194 |
| 6,083,222 A | 7/2000 | Klein et al. |
| 6,096,021 A | 8/2000 | Helm et al. |
| 6,123,699 A | 9/2000 | Webster, Jr. |
| 6,126,649 A | 10/2000 | VanTassel et al. |
| 6,126,654 A | 10/2000 | Giba et al. |
| 6,129,707 A | 10/2000 | Cryer |
| 6,129,708 A | 10/2000 | Enger |
| 6,146,338 A | 11/2000 | Gardeski et al. |
| 6,146,355 A | 11/2000 | Biggs |
| 6,169,916 B1 * | 1/2001 | West .......................... 600/373 |
| 6,183,435 B1 | 2/2001 | Bumbalough et al. |
| 6,183,463 B1 | 2/2001 | Webster, Jr. |
| 6,224,587 B1 | 5/2001 | Gibson |
| 6,238,389 B1 * | 5/2001 | Paddock et al. ............ 600/146 |
| 6,251,092 B1 * | 6/2001 | Qin et al. ................... 604/524 |
| 6,270,476 B1 * | 8/2001 | Santoianni et al. ...... 604/95.04 |
| 6,319,275 B1 * | 11/2001 | Lashinski et al. .......... 623/1.11 |
| 6,321,749 B1 | 11/2001 | Toti et al. |
| 6,582,536 B2 | 6/2003 | Shimada |
| 2001/0037084 A1 | 11/2001 | Nardeo |
| 2001/0039413 A1 | 11/2001 | Bowe |
| 2001/0049491 A1 | 12/2001 | Shimada |
| 2001/0049518 A1 | 12/2001 | Hoch |
| 2003/0109861 A1 | 6/2003 | Shimada |

* cited by examiner

MANIPULATABLE DELIVERY CATHETER FOR OCCLUSIVE DEVICES

FIELD OF THE INVENTION

This invention is in the general field of surgical instruments, and is specifically, a microballoon-tipped delivery catheter with a flexible, proximally-manipulated hinge region. The catheter may have a shaft of varying flexibility which contains several lumen. The inner, or delivery, lumen generally may be used with a guide wire to access target sites within the body through the flexible, small diameter vessels of the body. The delivery lumen may be also used for placement of occlusive materials, e.g., in an aneurysm. Inflation of the micro-balloon, located near the distal tip of the catheter, is effected using the inflation lumen. The push/pull wire lumen contains a wire, which when manipulated, flexes the catheter's distal tip.

BACKGROUND OF THE INVENTION

Endovascular therapy has been used to treat different conditions, such treatments including control of internal bleeding, occlusion of blood supply to tumors, and occlusion of aneurysm. Often the target site of the malady is difficult to reach. Because of their ability to access remote regions of the human body and deliver diagnostic or therapeutic agents, catheters are increasingly becoming components of endovascular therapies. Generally, catheters are introduced into large arteries, such as those in the groin or in the neck, and then pass through narrowing regions of the arterial system until the catheter's distal tip reaches the selected delivery site. To be properly utilized, catheters are often stiffer at their proximal end to allow the pushing and manipulation of the catheter as it progresses through the body but sufficiently flexible at the distal end to allow passage of the catheter tip through the body's blood vessels without causing significant trauma to the vessel or surrounding tissue.

Microcatheters, such as those shown in U.S. Pat. Nos. 4,884,579 and 4,739,768, each to Engleson, allow navigation through the body's tortuous vasculature to access such remote sites as the liver or the cerebral arteries of the brain. Although other methods of causing a catheter to proceed through the human vasculature exist (e.g., flow directed catheters), a guidewire-aided catheter is considered to be both quicker and more accurate than other procedures. Catheters with deflectable or variable stiffness distal ends (which increase the flexibility of the catheter's distal end) have been disclosed in U.S. Pat. No. 6,083,222, to Klein et al; U.S. Pat. No. 4,983,169, to Furukawa; U.S. Pat. No. 5,499,973, Saab; and U.S. Pat. No. 5,911,715, to Berg et al.

The addition of a fluid-expandable balloon on the distal end of the catheter and a coupler on the proximal end allows various percutaneous medical treatments such as pressure monitoring, cardiac output and flow monitoring, angioplasty, artificial vaso-occlusion, and cardiac support. Balloon catheters generally include a lumen that extends from the proximal end and provides fluid to the balloon for inflation. Examples of balloon catheters are disclosed in U.S. Pat. No. 4,813,934 to Engleson et al and U.S. Pat. No. 5,437,632 to Engelson et al. A balloon catheter with an adjustable shaft is shown in U.S. Pat. No. 5,968,012, to Ren et al.

For certain vascular malformations and aneurysms, it may be desirable to create an endovascular occlusion at the treatment site. A catheter is typically used to place a vaso-occlusive device or agent within the vasculature of the body either to block the flow of blood through a vessel by forming an embolus or to form such an embolus within an aneurysm stemming from the vessel. Formation of an embolus may also involve the injection of a fluid embolic agent such as microfibrillar collagen, Silastic beads, or polymeric resins such as cyanoacrylate. Ideally, the embolizing agent adapts itself to the irregular shape of the internal walls of the malformation or aneurysm. Inadvertent embolism due to an inability to contain the fluid agent within the aneurysm is one risk which might occur when using fluid embolic agents.

Mechanical vaso-occlusive devices may also be used for embolus formation. A commonly used vaso-occlusive device is a wire coil or braid which may be introduced through a delivery catheter in a stretched linear form and which assumes an irregular shape upon discharge of the device from the end of the catheter to fill an open space such as an aneurysm. U.S. Pat. No. 4,994,069, to Ritchart et al, discloses a flexible, preferably coiled, wire for use in a small vessel vaso-occlusion.

Some embolic coils are subject to the same placement risks as that of fluid embolic agents in that it is difficult to contain the occlusive coil within the open space of the aneurysm. A need exists for a delivery system which accurately places the occluding coil or fluid and ensures that the occluding coil or fluid does not migrate from the open space within the aneurysm. The delivery catheter must have a small diameter, have a highly flexible construction which permits movement along a small-diameter, tortuous vessel path, have a flexible method of placement to ensure accuracy, and must have a method to prevent coil or embolizing agent leakage.

SUMMARY OF THE INVENTION

This invention is a catheter or catheter section having: a balloon region located from distal of an inflatable member to proximal of an inflatable member, where the inflatable member is within the balloon region, a flexible joint region within that balloon region, and a wire configured to flex the flexible joint region. The flexible joint may variously be distal of the inflatable member, within the inflatable member, or proximal of said inflatable member. The flexible joint region preferably has a flexibility of up to 90° in either direction. The flexible joint itself may be, for instance, a coil member, perhaps having a section with a pitch which is larger than adjacent coil pitches. The flexible joint may instead be a braid, perhaps with a section with a pic which is larger than the pic of one or more adjacent sections. The flexible joint may also be made up of a polymer tubing with a section which is softer than adjacent tubing polymers or a region having a wall thickness that is thinner than adjacent wall thickness.

The inflatable member or balloon may be of a material selected from the group consisting of elastomers such as silicone rubber, latex rubber, natural rubber, butadiene-based co-polymer, EPDM, and polyvinyl chloride or thermoplastic polymers such as polyethylene, polypropylene, and Nylon.

DESCRIPTION OF THE INVENTION

Figures 1A, 1B, 1C:
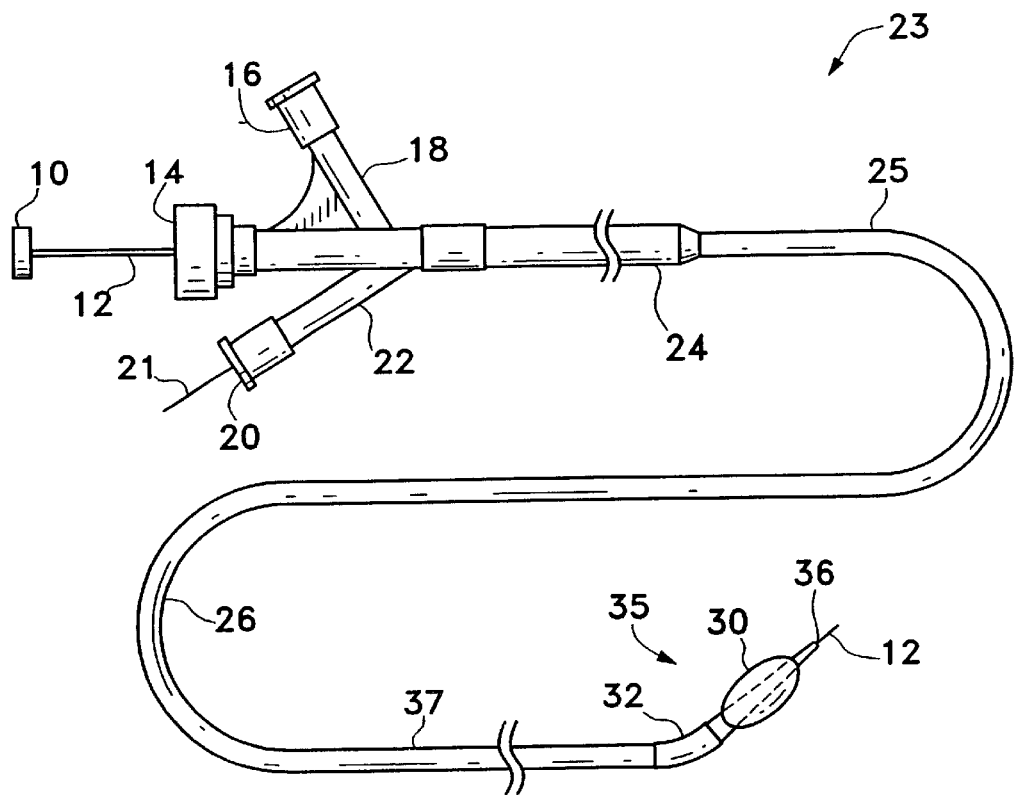
FIG. 1 is an external view of one variation of the inventive catheter device.

This invention involves a multi-lumen, single-balloon catheter for the delivery of vaso-occlusive materials or implants. The device is shown in detail in the figures wherein like numerals indicate like elements. The catheter preferably includes a shapeable, flexible distal section in the vicinity of the balloon. The flexible section, or "hinge region", preferably is manipulated from outside the body during the process of delivering the vaso-occlusive device or material. The terms "hinge region", "hinge", or "flexible joint" may be used interchangeably for our applications.

FIG. 1 shows a catheter assembly 23 made according to one variation of the invention. This variation of the catheter assembly 23 includes a catheter shaft 25 composed of a flexible, thin walled body or tube 26 having an inner lumen which extends between proximal and distal catheter ends 24, 37, respectively. The tube 26 is preferably a generally nondistensible polymer having the appropriate mechanical properties for this application, and preferably polyethylene (e.g., HDPE, LDPE, LLDPE, MDPE, etc.), polyesters (such as Nylon), polypropylene, polyimide, polyvinyl chloride, ethylvinylacetate, polyethylene terephthalate, polyurethane (e.g. Texin such as that made by Bayer Corporation), PEBAX, fluoropolymers, mixtures of the aforementioned polymers, and their block or random co-polymers.

The catheter assembly generally has several overall functions: access through the vasculature to the brain often, but not necessarily, using a guide wire; inflation of the inflatable member or balloon to close or to restrict an artery or the mouth of an aneurysm prior to or during placement of a vaso-occlusive device, thereby requiring a fluid pathway for inflation of the inflatable member; flexion at a "hinge region" in the neighborhood of the distal end of the catheter by a wire extending proximally through the catheter; and introduction of a vaso-occlusive device or material for eventual placement in the vasculature, thereby requiring a pathway or storage region for the vaso-occlusive device. These functions may be achieved by features found at the proximal and distal regions of the catheter.

The proximal catheter end 24 may be provided with a fitting 18 (e.g., a "LuerLok") through which fluid may be supplied to the catheter's inflation lumen through a side port 16. The proximal end of the catheter is provided with a second port 20 and a fitting 22 through which a push/pull wire may be used to manipulate the hinge region 32 in the distal catheter tip. The proximal end fitting 18 includes an axially extending port 14 which communicates with the catheter's delivery/guide wire lumen. The optional guide wire 12 may have any suitable construction for guiding the flexible catheter to its intended site within the body. The proximal end of the guide-wire 12 may be equipped with a handle 10 for applying torque to the guide wire 12 during catheter operation. The guide-wire may have a variable stiffness or stepped diameter along its length which typically, e.g., a larger-diameter, stiffer proximal region and one or more smaller-diameter, more flexible distal regions.

The distal portion 35 of the catheter is made of an inflatable member 30, typically a balloon, a hinge region 32, and an opening or aperture 36 for delivery of the vaso-occlusive device or material. This opening 36 may also be used for delivery of drugs and the vaso-occlusive device to the selected vascular site. The distal end region 35 of the catheter 25 is provided with an inflatable balloon 30 which, when inflated, aids in the placement of vaso-occlusive materials or devices by blocking the entrance to the aneurysm or the artery adjacent to the aneurysm.

The balloon wall section (discussed in greater detail below) is preferably formed from a thin sleeve of polymeric material and attached at its opposite sleeve ends to a relatively more rigid tube section. FIGS. 1A, 1B, and 1C display various configurations of the distal catheter tip 35 positioning based on the placement of the flexible hinge region. FIGS. 1A, 1B, and 1C respectively show variations of the inventive catheter 23 in which the hinge region 32 is placed proximal to (FIG. 1A), within (FIG. 1B), and distal to (FIG. 1C) the inflatable member region 30. Flexion of the hinge region is achieved through remote manipulation of the push/pull wire 21.

FIGS. 2A through 2D illustrate variations of the distal end region 35 and hinge region 32 of the catheter illustrated in FIGS. 1A, 1B, and 1C.

Figure 2A:
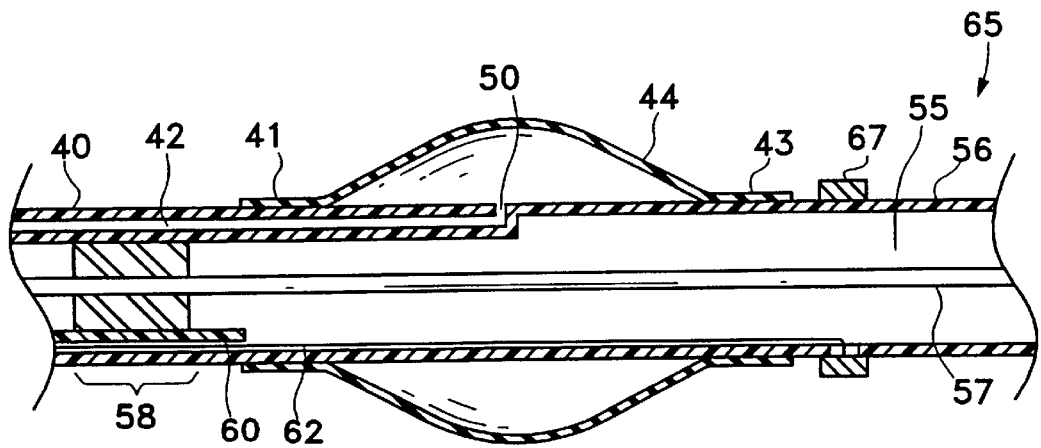
FIG. 2A shows a cross sectional view of a proximally placed hinge region in a variation of the distal region of the inventive catheter.
Figure 2B:
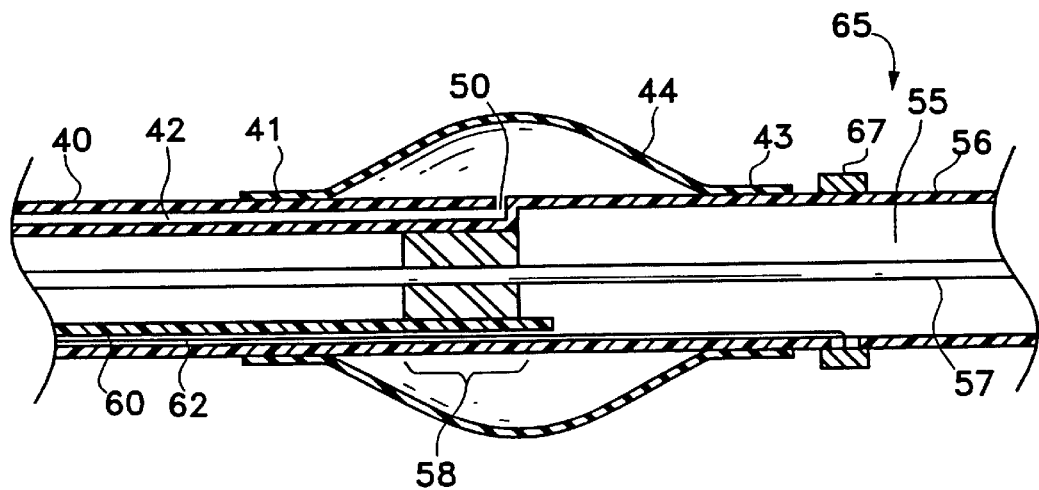
FIG. 2B shows a cross sectional view of a mid-balloon hinge region placement for a variation of the distal region of the inventive catheter.

The catheter tube 40 of FIG. 2A has an inflatable member 44, preferably a balloon, which is formed by an inflatable sleeve secured at its ends 41, 43 to the catheter tube wall 40. The inflatable member or balloon 44 may be of a shape, thickness, and material as is typical of balloons used in neurovascular balloon catheters. Preferably, though, the inflatable member or balloon 44 is formed of a thin polymeric material, and preferably an elastomeric, stretchable material such as silicone rubber, latex rubber, polyvinyl chloride, complex co-polymers such as styrene-ethylene butylene-styrene copolymers such as C-FLEX, or alternatively, a non-stretchable film material such as polyethylene, polypropylene, or polyamides such as Nylon. Attachment of the sleeve ends to the catheter tube may be by gluing, heat shrinkage, mechanical fastener, or other suitable method. The inflation lumen 42 allows communication between the inflation fluid source and the balloon 44 through at least one opening 50 formed in the catheter tube 40. Inflation and deflation of the balloon are effected by the passage of radioopaque fluid, saline, or other fluid. The push/pull wire lumen 60 extends throughout the catheter tube 40 and protects the passage of the push/pull wire 62 which is connected to the inner wall of the catheter tube 40. To assist in preventing collapse of the tube 60 enclosing the push/pull wire 62 and to prevent kinking or bulging during actuation, the push/pull wire lumen 60 may have additional structure preferably provided by a layer of higher stiffness polymer (e.g., a polyimide), a support coil, or a support braid.

Manipulation of the push/pull wire 62 via the proximal wire port (20 in FIG. 1A) allows flexion of the distal end 35 of the catheter (25 in FIG. 1A). The guide wire 57 extends through the delivery lumen 55 which lies interior to the catheter tube 40. The push/pull wire 62 extends through the push/pull wire lumen 60 and may be bonded to the platinum band 67 which surrounds the catheter's distal end 65. The hinge region 58 at which the distal catheter tip 65 flexes due to proximal manipulation of the push/pull wire 62 may be located proximal to, within, or distal to the balloon, as displayed respectively in FIGS. 2A, 2B, and 2C.

Figure 2C:
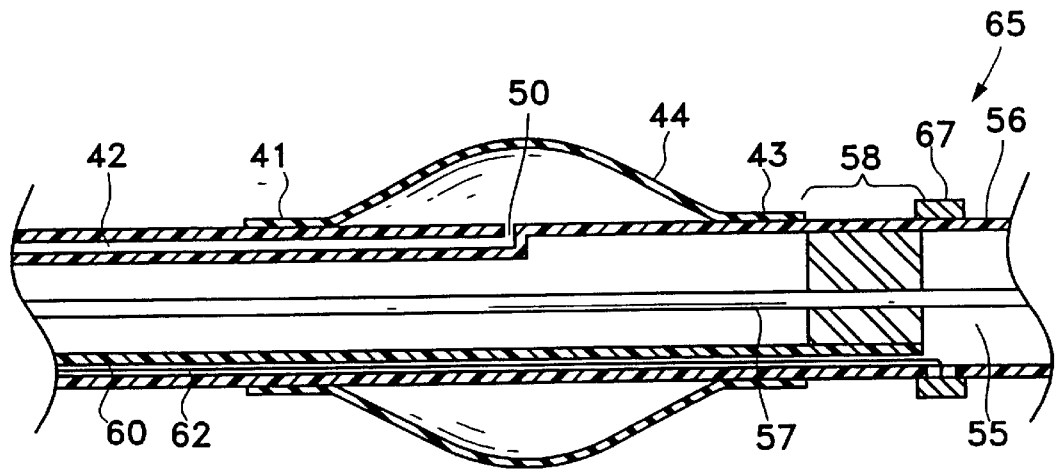
FIG. 2C shows a cross sectional view of a distally placed hinge region in a variation of the distal region of the inventive catheter.

As shown in FIG. 2A, when the hinge region 58 is placed proximally of the balloon 44, the push pull wire lumen 60 extends to a region which is proximal of the distal end of the balloon 44 to allow flexion of the region of the catheter's distal end 65 which includes the entire balloon 44. If the hinge region 58 is placed interior to the balloon, as in FIG. 2B, flexion of the catheter's distal end 65 occurs such that the point of flexion is within the balloon (also displayed in FIG. 1B). FIG. 2C shows the placement of hinge 58 distal to the balloon; flexion during distal-hinge placement occurs such that the manipulatable region of the catheter's distal end 65 does not include any portion of the balloon 44.

Figure 2D:
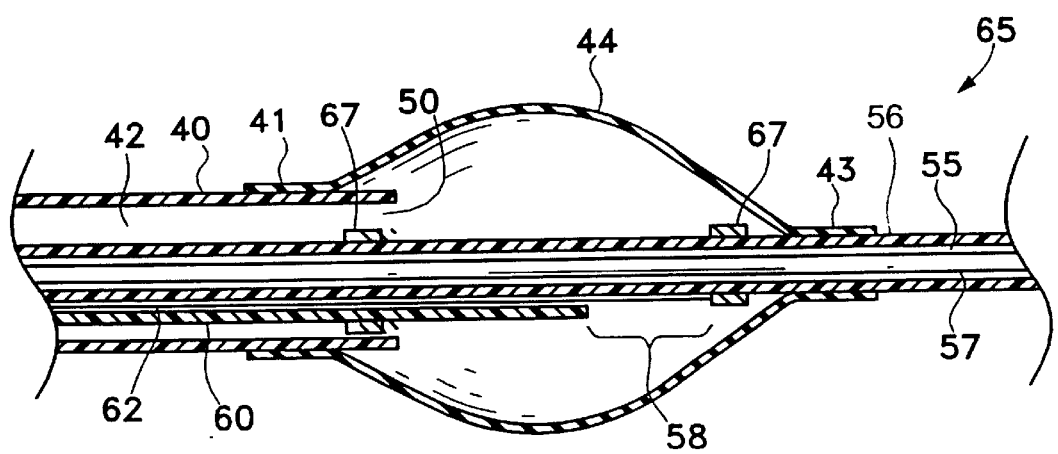
FIG. 2D shows a cross sectional view of an additional mid-balloon hinge region placement for one variation of the distal region of the inventive catheter.

FIG. 2D shows placement of the hinge region 58 interior to the balloon 44. The balloon 44 extends between the guidewire/delivery tube 56 and the outer catheter tube 40 enclosing the annular inflation lumen 42. The push/pull wire 62 is attached to the distal end 65 of the guidewire/delivery lumen tube 56.

In each of the variations shown in FIGS. 2A, 2B, 2C, and 2D, the push/pull wire 62 is distally attached to a radio-opaque band 67. Although this is a preferred variation, other attachment sites for attachment of the push/pull wire 62 distal to the hinge region 58 will be apparent.

The hinge region may be made up of any material or structural configuration which allows flexion based on remote manipulation by movement of the push/pull wire 62. Several variations of preferred configuration are shown in FIGS. 2D, 3A, 3B, and 3C.

In FIG. 2D, extension of the delivery lumen tube 56 beyond the end of the inflation lumen 42 allows remote manipulation of the catheter's distal end 65 if the push/pull wire 62 is attached to a marker or platinum band 67 which is located distal to the end of the inflation lumen. In this configuration, remote manipulation of the push/pull wire allows flexion to occur between the end of the inflation lumen 42 and the marker 67 to which the push/pull wire 62 is attached. The delivery lumen tube 56 may be made of any of the materials listed above with respect to tube 26 in FIG. 1.

Figure 3A:
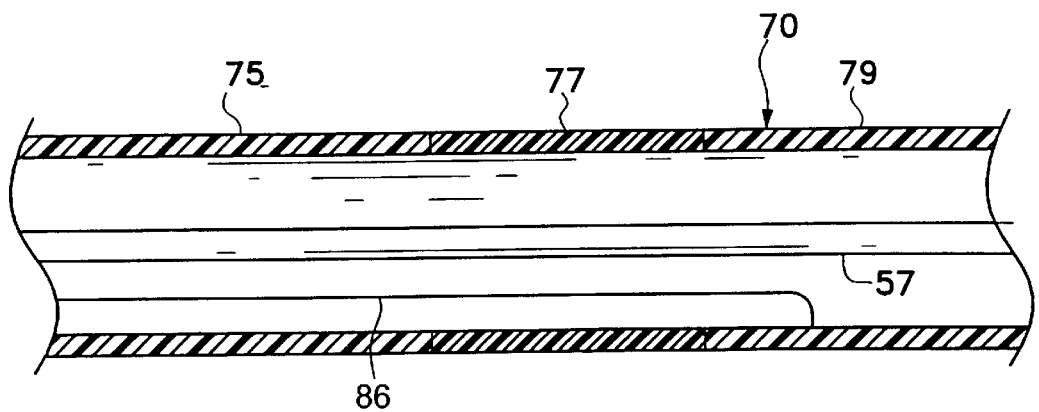
FIG. 3A shows a cross-sectional view of an alternate hinge region construction for the distal region of the inventive catheter. The hinge region of FIG. 3A is composed of a section of material which is surrounded by regions of greater stiffness.

FIG. 3A displays a cross section of the catheter 70 wall. The hinge section of FIG. 3A is made from contiguous regions of tubing where one section of the catheter wall 77 is made from a material with a stiffness which is less than the stiffness of the material of the flanking sections of catheter wall 75, 79. These regions of tubing are preferably made through extrusion, by doping, or heat treating a region of the tubing.

Figure 3B:
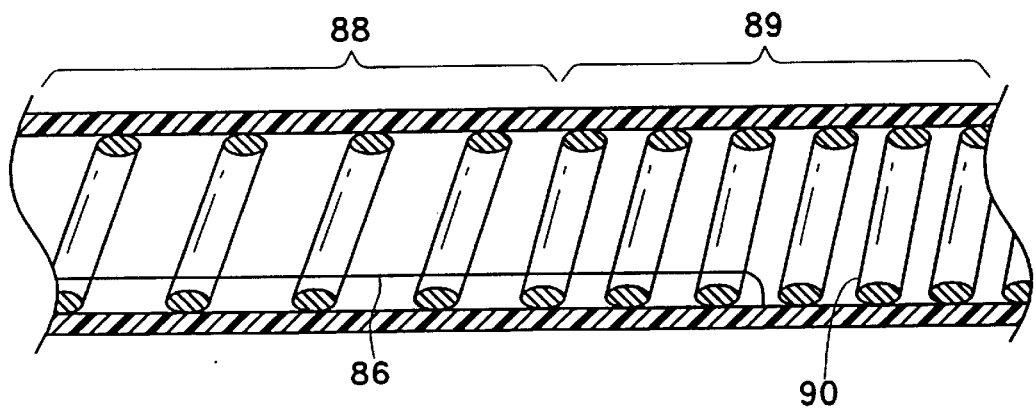
FIG. 3B shows a cross-sectional view of an alternate hinge region construction for the distal region of the inventive catheter. The hinge region of FIG. 3B is composed of a coil of varying pitch.

FIG. 3B displays a hinge region 88 which utilizes a coil 90 of varying pitch imbedded in the catheter wall. Because the variation in pitch of the coil 90 produces regions of varying flexibility, the lower pitch region 88 is more flexible than the region of higher pitch 89. The higher pitch region 89 is stiffer during manipulation of the push/pull wire 86.

Figure 3C:
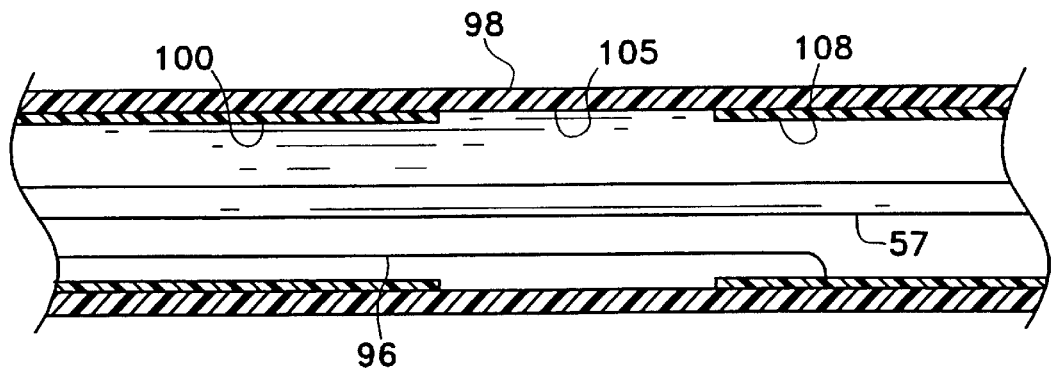
FIG. 3C shows a cross-sectional view of an alternate hinge construction for the distal region of the inventive catheter. The hinge of FIG. 3C is composed of a region of thinned tubing wall surrounded by regions of thickened tubing wall.

As shown in FIG. 3C, if a thinned region of catheter wall 105 is flanked by regions of greater wall cross-sectional area 100, 108, the section 108 of the catheter wall which is distal to the thinned section 105 will act as a hinge when the distal end of the catheter is manipulated using the push/pull wire 96. The variations in wall cross sectional area may preferably be created during an extrusion process.

Figure 3D:
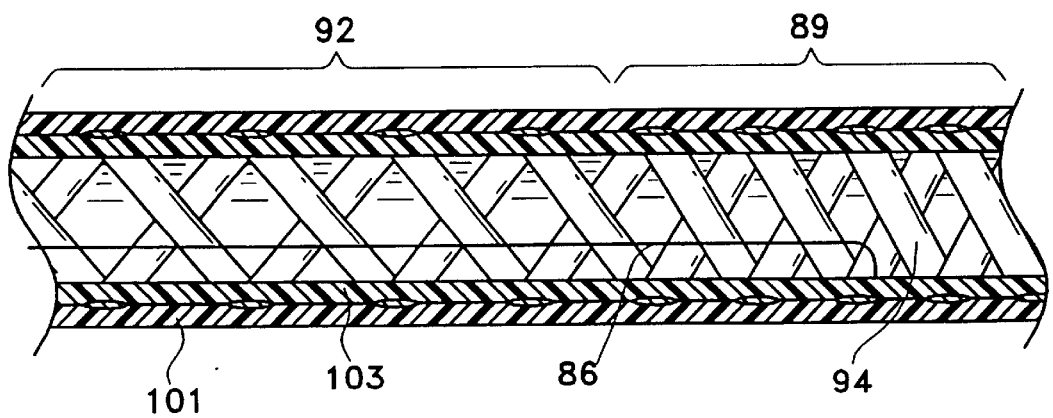
FIG. 3D shows a cross-sectional view of an alternate hinge region construction for the distal region of the inventive catheter. The hinge region of FIG. 3B is composed of a braided region which is flanked by regions of higher braid density.

FIG. 3D displays a hinge which utilizes a braided ribbon 94 with varying braid pitch, that is embedded between outer 101 and inner 103 layers of the catheter wall. The variation in pitch of the braided ribbon 105 produces regions of varying flexibility. If a region of lower braid pitch 92 is flanked by regions of higher braid pitch 90, the region of greater pitch 90 is stiffer during during manipulation of the distal catheter tip. The metallic braid 94 is preferably made from a number of metallic ribbons or wires which are members of a class of alloys known as super-elastic alloys, but may also be made from other appropriate materials such as stainless steel or polymers such as liquid crystal polymers (LCP's). Preferred super-elastic alloys include the class of titanium/nickel materials known as nitinol. Additional treatment to the braid prior to assembly, such as heat-treatment, may be required or desired to prevent braid unraveling, changes in diameter, or spacing during handling. The braids which may be utilized in this invention are preferably made using commercially available tubular braiders. The term "braid" is meant to include tubular constructions in which the ribbons making up the construction are woven radially in and in-and-out fashion as they cross to form a tubular member defining a single lumen. The braid is preferably made from a suitable number of ribbons or wires.

Figure 4A:
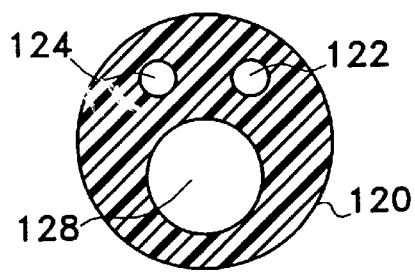
FIGS. 4A–4H are cross-sectional views of catheter shafts displaying the various relative positions of the push/pull wire lumen, inflation lumen, and delivery lumen.
Figure 4B:
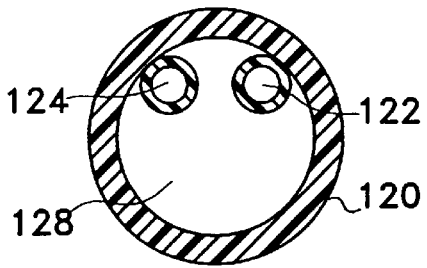
Figure 4C:
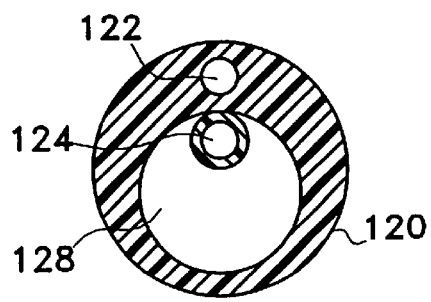
Figure 4D:
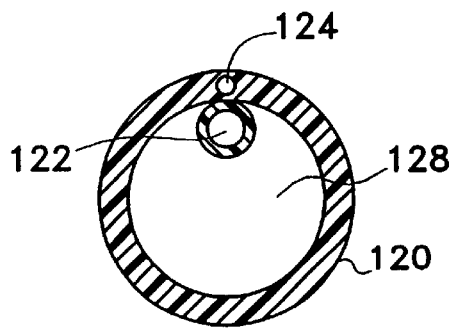
Figure 4E:
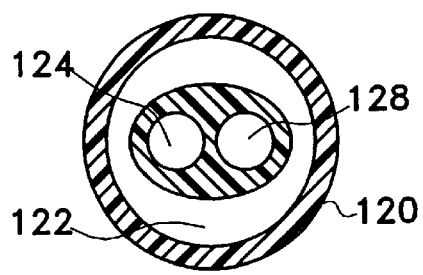
Figure 4F:
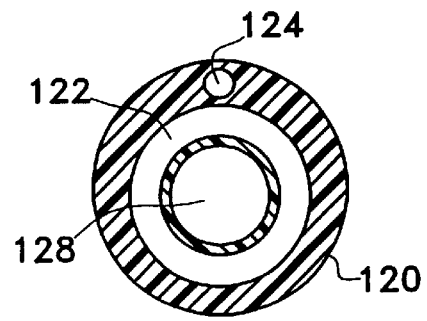
Figure 4G:
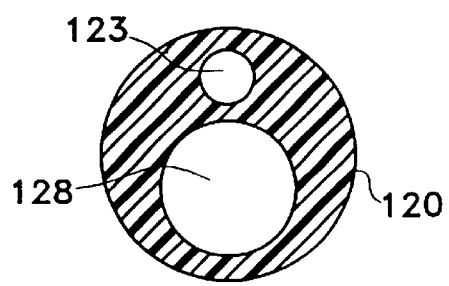
Figure 4H:
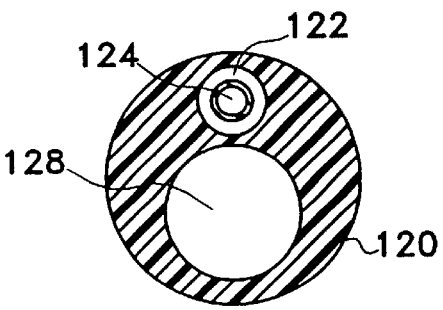

Some of the various configurations of the catheter's lumina (inflation, push/pull, and delivery) are displayed in FIGS. 4A through 4H. In FIG. 4A, the inflation lumen 122 and push/pull wire lumen 124 are formed interior to the catheter wall 120, while the interior catheter wall forms the guide wire lumen 128. In FIG. 4B, the catheter wall 120 forms the guide wire lumen 128 which contains the inflation lumen 122 and push/pull wire lumen 124. The inflation lumen 122 is formed interior to the catheter wall 120 of FIG. 4C, while the push/pull wire lumen 124 lies within the larger coil lumen 128 (which is formed by the catheter wall 120). FIG. 4D is a variation of FIG. 4C in which the push/pull wire lumen 124 lies interior to the catheter wall 128 while the inflation lumen 122 lies within the larger coil lumen 128. In FIG. 4E, the interior catheter wall 120 forms the inflation lumen 122, and the push/pull wire lumen 124 and the guide wire lumen 128 are found within the inflation lumen 122. The inflation lumen 122 surrounds the guide wire lumen 128 and lies within the region formed interior catheter wall 120 in FIG. 4F, while the push/pull wire lumen 124 lies within the catheter wall 120. In FIG. 4G, one shared lumen 123 serves as the push/pull and inflation lumen; the shared push/pull and inflation lumen 123 along with the guide wire lumen 128 lie within the catheter wall 120. Another alternate variation of the lumina positioning, shown in FIG. 4H, has the push/pull wire lumen 124 lying interior to the inflation lumen 122 which is contained within the catheter wall 120, while a separate lumina for the guide wire 128 also is contained within the catheter wall.

The tube constructions, hinge region construction, and other tubing forming the various lumina discussed herein may be created through extrusion, sequential production (in which the parts are manufactured separately and later assembled together), or some other method.

Figure 5:
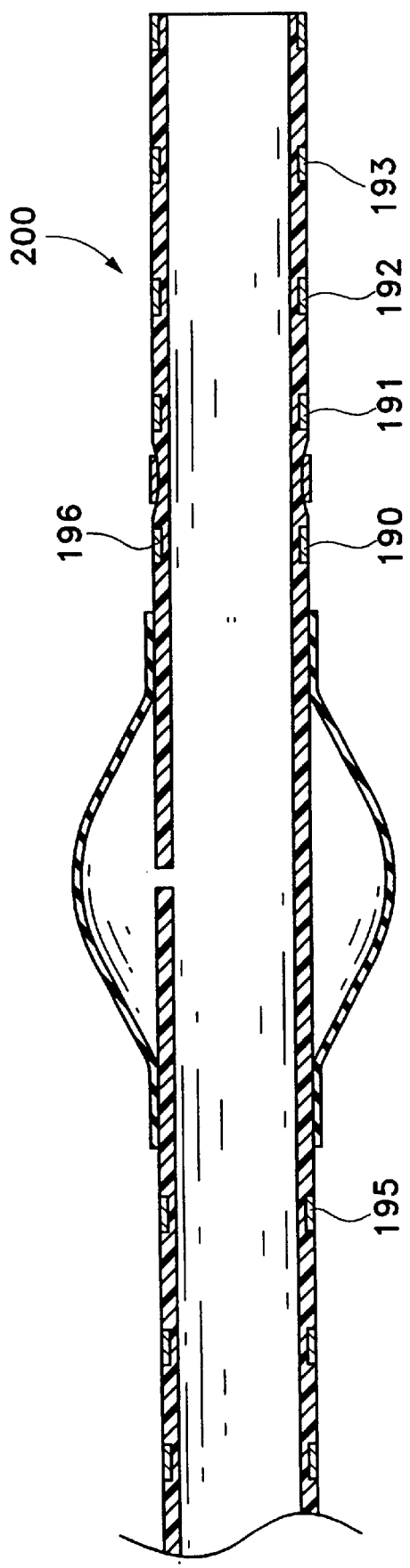
FIG. 5 shows the positions of the radioopaque markers positioned within the distal end of the catheter tip.

As displayed in FIG. 5, another variation of the present invention may involve the addition of radioopaque makers 190. The lengthened distal section 200 may be provided with a number of spaced radioopaque markers 190, 191, 192, and 193. Balloon markers 195, 196 may be provided to indicate the position of the balloon during the vascular procedure. The markers may be spaced, for instance, such that the inter-marker distance corresponds to the length of the coil to be delivered.

Figure 6A:
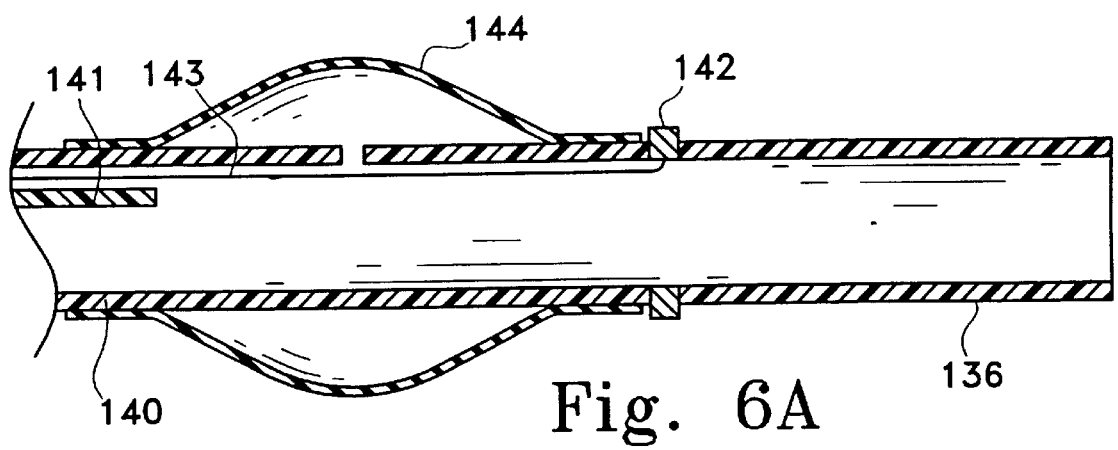
FIG. 6A shows the relative position of the distal end of the catheter tip when not flexed.
Figure 6B:
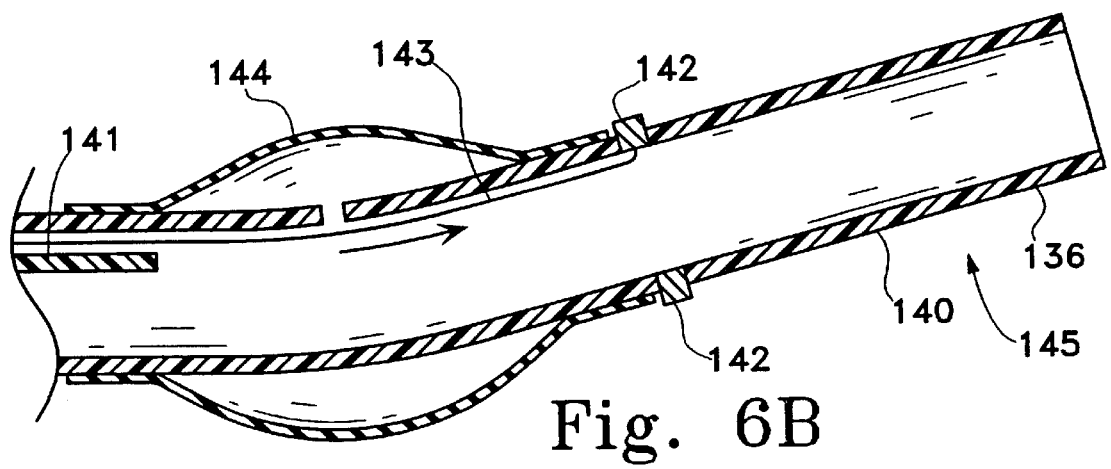
FIG. 6B shows the relative position of the distal end of the catheter when flexed by pulling the push/pull motion wire.
Figure 6C:
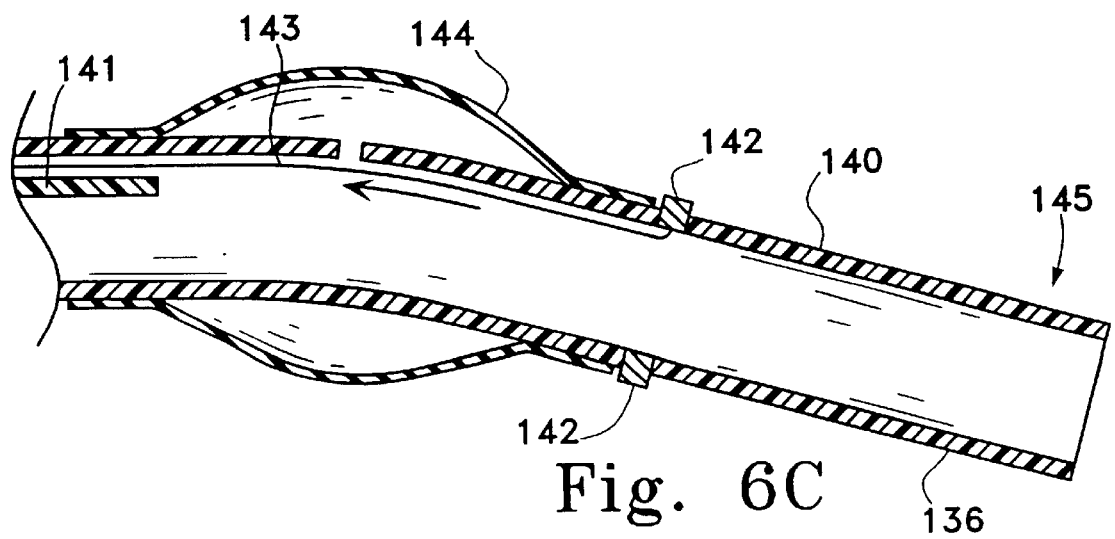
FIG. 6C shows the relative position of the distal end of the catheter when flexed by pushing the push/pull motion wire.

FIGS. 6A, 6B, and 6C show the operation of the inventive flexible distal catheter tip.

In FIG. 6A, the remotely-manipulatable distal end 136 extends beyond the hinge 135 and allows greater access to the delivery site of the vaso-occlusive member 137 during surgical procedures. Manipulation of the push/pull wire 143 allows flexion of the catheter distal tip 136.

If the push/pull wire 143 is pushed, as shown in FIG. 6B, the distal tip 145 is flexed upward through an angle determined by the pressure applied to the push/pull wire. Generally, the deflection angle of the catheter 140 as the push/pull wire 143 is pushed approaches 90° in one direction.

If the push/pull wire 143 is pulled as in FIG. 6C, rotation from the un-manipulated position through an angle up to 90° opposite the direction shown in FIG. 6B is initiated; again, this angle is in a direction which is opposite to that of the pull-manipulation but generally in the same plane. The push/pull wire 143 extends through out the push/pull wire lumen 141 and may be bonded to the radioopaque band 142 found at the distal end 145 of the catheter 140 tip.

A remotely flexible distal tip is particularly useful when treating an aneurysm by placement of a vaso-occlusive device or material in the aneurysm. FIGS. 7A–7D depict such a placement.

Figure 7A:
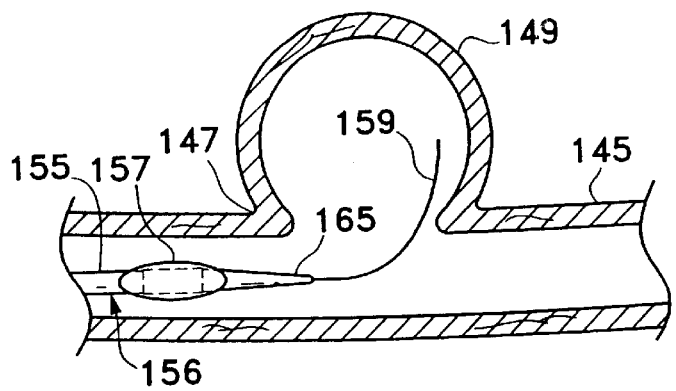
FIGS. 7A, 7B, 7C, and 7D show the steps of using the inventive catheter by respectively inserting the distal end of the inventive catheter into a blood vessel, placing a vaso-occlusive device within an aneurysm, and removing of the catheter.

FIG. 7A displays an inventive catheter 156 that has its distal end positioned outside the mouth of an aneurysm 149 to deliver a vaso-occlusive coil. The device is positioned using a guidewire 159.

Figure 7B:
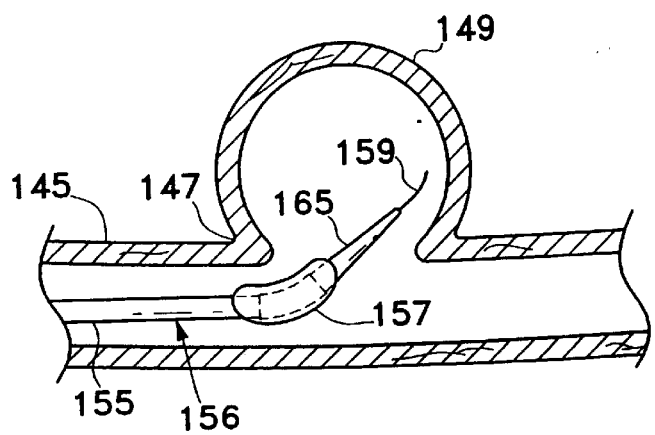
Figure 7C:
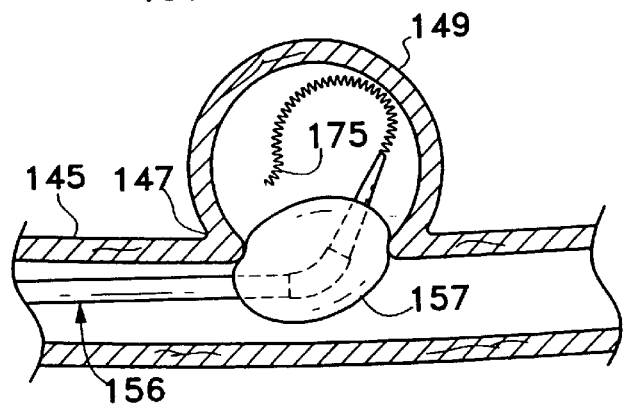
Figure 7D:
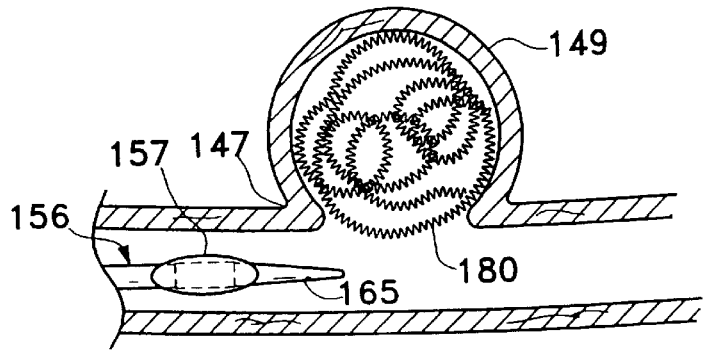

Introduction of the catheter's distal end 165 into the aneurysm neck 147, shown in FIG. 7B, displays the advantages of the inventive remotely manipulatable catheter. Flexion of the catheter's distal tip using the push/pull wire allows for greater maneuverability when accessing the aneurysm neck and aneurysm sac. The push/pull wire system allows the distal end to be positioned as desired during the procedure, instead of before the procedure begins. Once the distal tip 165 has been properly positioned in the aneurysm neck 147, inflation of the balloon 170 is then commenced to occlude the aneurysm neck 147, as shown in FIG. 7C. Full occlusion of the aneurysm neck is desirable to ensure that the coils 175 do not escape into the vessel when the coils are discharged into the aneurysm sac 149. Once the coil or coils 175 have been completely discharged 180 into the aneurysm sac 149, deflation of the balloon 157 allows retraction 185 of the catheter's distal end from the aneurysm (shown in FIG. 7D).

The applications of the inventive catheter discussed above are not limited to the treatment of aneurysms, but may include any number of vascular maladies. Modification of the above-described methods for carrying out the invention, and variations of the mechanical aspects of the invention that are obvious to those of skill in the mechanical and guide wire and/or catheter arts are intended to be within the scope of the claims.

I claim as my invention:

1. A catheter section comprising:
   a.) a balloon region having a main lumen and an inflatable member within said balloon region,
   b.) a flexible joint region within said balloon region, and
   c.) a push/pull wire having a distal end secured to a radio-opaque band fixed to the catheter section, wherein the wire is configured to be pushed and pulled along a longitudinal axis of the wire through a wire lumen having an open distal end and adjacent to the main lumen to flex the flexible joint region.

2. The catheter section of claim 1 wherein the flexible joint is distal of said inflatable member.

3. The catheter section of claim 1 wherein the flexible joint is within said inflatable member.

4. The catheter section of claim 1 wherein the flexible joint is proximal of said inflatable member.

5. The catheter section of claim 1 wherein the flexible joint region has a flexibility of up to 90° relative to a longitudinal axis of the catheter assembly.

6. The catheter section of claim 1 wherein the flexible joint comprises a coil member.

7. The catheter section of claim 6 wherein the coil member has a section with a pitch which is larger than adjacent coil pitches.

8. The catheter section of claim 1 wherein the flexible joint comprises a braid.

9. The catheter section of claim 8 wherein the braid has a section with a pic which is larger than adjacent pics.

10. The catheter section of claim 1 wherein the flexible joint is comprised of a polymer which is softer than adjacent polymers.

11. The catheter section of claim 1 wherein the flexible joint is a region having a wall thickness that is thinner than adjacent wall thickness.

12. The catheter section of claim 1 wherein the inflatable m ember comprises a material selected from the group consisting of elastomers and thermoplastic polymers.

13. The catheter section of claim 12 wherein said material is an elastomer.

14. The catheter section of claim 13 wherein said elastomer is selected from the group consisting of silicone rubber, latex rubber, natural rubber, butadiene-based co-polymers, EPDM, polyvinyl chloride, and complex co-polymers such as styrene-ethylene butylene-styrene co-polymers.

15. The catheter section of claim 13 wherein said elastomer is silicone rubber.

16. The catheter section of claim 12 wherein the said material is a thermoplastic polymer.

17. The catheter section of claim 16 wherein thermoplastic polymer is selected from polyethylene, polypropylene, and Nylon.

18. The catheter section of claim 1 further comprising a guidewire disposable within a lumen defined through a length of the catheter section balloon region.

19. The catheter section of claim 18 wherein the guidewire has a variable stiffness along its length.

20. The catheter section of claim 18 wherein the guidewire has a stepped diameter along its length.

21. The catheter section of claim 1 wherein the catheter section defines a lumen therethrough.

22. The catheter section of claim 21 wherein the catheter section defines an opening at a distal end of the catheter section which is in communication with the lumen.

23. The catheter section of claim 1 wherein the wire is disposed within the wire lumen defined through a length of the catheter section.

24. The catheter section of claim 1 further comprising at least one radio-opaque marker disposed along the catheter section for indicating a position of the inflatable member.

25. A catheter assembly for delivering a vaso-occlusive member comprising:
   a.) an inner tubing member having a lumen and extending between a proximal and a distal end of the catheter;
   b.) a guidewire insertable through and removable from said inner tubing lumen and which guidewire is suitable for guiding the catheter when the catheter is advanced through a hollow body organ;
   c.) an inflation member in fluid communication with an inflation lumen defined in the catheter;
   d.) a push/pull wire attached within the catheter, wherein the push/pull wire is adapted to be pushed and pulled along a longitudinal axis of the wire through a wire lumen having an open distal end and adjacent to the lumen of the inner tubing member; and
   e.) a flexible joint region defined along the catheter which is manipulatable via pushing and/or pulling the wire.

26. The catheter assembly of claim 25 wherein the guidewire has a variable stiffness along its length.

27. The catheter assembly of claim 25 wherein the guidewire has a stepped diameter along its length.

28. The catheter assembly of claim 25 wherein the joint region has a flexibility of up to 90° relative to a longitudinal axis of the catheter assembly.

29. The catheter assembly of claim 25 further comprising f.) a length of vaso-occlusive coil configured for delivery through the catheter assembly.

* * * * *